(12) United States Patent
Lien

(10) Patent No.: US 7,362,274 B1
(45) Date of Patent: Apr. 22, 2008

(54) COUPLED FEED-IN BUTTERFLY SHAPED LEFT/RIGHT HAND CIRCULARLY POLARIZED MICROSTRIP ANTENNA

(76) Inventor: Huan-Cheng Lien, No. 13, Alley 36, Lane 457, Siping Rd., Douliou City, Yunlin County 640 (TW)

( * ) Notice: Subject to any disclaimer, the term of this patent is extended or adjusted under 35 U.S.C. 154(b) by 0 days.

(21) Appl. No.: 11/563,682

(22) Filed: Nov. 28, 2006

(51) Int. Cl.
*H01Q 1/38* (2006.01)
(52) U.S. Cl. .............................. 343/700 MS; 343/750
(58) Field of Classification Search .......... 343/700 MS
See application file for complete search history.

(56) References Cited

U.S. PATENT DOCUMENTS 7,274,273 B2 * 9/2007 Hirose et al. ............... 333/134

2007/0188384 A1 * 8/2007 Liu ...................... 343/700 MS

* cited by examiner

*Primary Examiner*—Trinh Vo Dinh

(57) ABSTRACT

A coupled feed-in butterfly shaped left/right hand circularly polarized microstrip antenna includes a delta resonator, a butterfly shaped radiator, an elongated rectangular feed line, a connecting sheet, a cylindrical conductor, a signal receiving adapter, and a feed-in terminal. All the above components are disposed in parallel in the three dimensional space. The butterfly shaped radiator has a cavity formed at the position corresponding to the delta resonator. A pair of front wing tips and a pair of rear wing tips are respectively formed symmetrically at the front corners and the rear corners of the butterfly shaped radiator. The elongated rectangular feed line is electrically connected to the butterfly shaped radiator with the connecting sheet, and the cylindrical conductor is facing to a circular hole formed on the butterfly shaped radiator in the manner able to adjust the impedance bandwidth. With this structure, a left/right hand circularly polarized microstrip antenna having broader impedance and axial ratio bandwidth can be obtained.

3 Claims, 9 Drawing Sheets

COUPLED FEED-IN BUTTERFLY SHAPED LEFT/RIGHT HAND CIRCULARLY POLARIZED MICROSTRIP ANTENNA

BACKGROUND OF THE INVENTION

1. Field of the Invention

The present invention relates to a technique of coupled feed-in circularly polarized microstrip antenna, and more particularly, to a left/right hand circularly polarized microstrip antenna capable of adjusting the impedance bandwidth so as to realize a broader impedance and axial ratio bandwidths.

2. Description of the Prior Art

Recently, there have been marvelous progresses in the products and the study of related hardware and software technique of the wireless communication. For efficiently operating wireless communication facilities in the modern stationary wireless communication system to transmit a large amount of audio and video data, there are still room for further improvement of the related hardware and software techniques.

In keeping pace with the rapid development of internet, the needs of broad band communication increase very eagerly. For example, the local multiple distribution service (LMDS) in the wireless broad band area provides a collaborated mutual broad band transmission medium which not only performs combined audio and video transmission nowadays but also has the opportunity to take over the place of the traditional domestic wired telephone so as to become wireless indoor telephone means.

As the microstrip antenna is very small in size, it is most suitable for micromechanical engineering, wherein its merits of compactness, light weight, and thin thickness curtail the production cost a lot. The present wireless communication and the global positioning system (GPS) should be operable at low cost that brings about the importance of the frequency variable microstrip antenna.

In a conventional microstrip antenna, the characteristic of operation in the narrow bandwidth is an important factor. On the other hand, except single feed-in circular polarization, its limitation in bandwidth is always affected by the resonance of the input impedance. Therefore, how to widen the bandwidth or develop variable frequency for the microstrip antenna, adjusting the broadband impedance matching is inevitable.

SUMMARY OF THE INVENTION

It is an object of the present invention to provide a coupled feed-in butterfly shaped left/right hand circularly polarized microstrip antenna having a cylindrical conductor to adjust the impedance bandwidth by varying its length or diameter.

It is another object of the present invention to provide a coupled feed-in butterfly shaped left/right hand circularly polarized microstrip antenna constructed of simplified figure and size collaborated with a size adjustable cylindrical conductor so as to vary the bandwidth of the antenna.

To achieve the aforesaid objects, the antenna of the present invention is formed among a first, a second, and a third dielectric substrates disposed in the three dimensional space and comprises the following components.

A delta resonator is made by etching a conducting metallic substance formed on the upper surface of the first dielectric substrate.

A butterfly shaped radiator is made by etching a conducting metallic substance formed beneath the lower surface of the first dielectric substrate, and a pair of front wing tips and a pair of rear wing tips are respectively formed symmetrically at the two front side corners and the two rear side corners thereof. Both kinds of wing tips are formed into an acute angle. At least one circular hole is formed between the two rear wing tips. A delta shaped cavity is opened in the middle of the butterfly shaped radiator, and a vertex angle is formed on the butterfly shaped radiator in front of the delta shaped cavity.

An elongated rectangular parallelepiped feed line is made by etching a conducting metallic substance formed on the upper surface of the second dielectric substrate, a joint terminal and a joint hole are formed at its one end, and a signal receiving node is formed at the other end thereof.

A connecting sheet is disposed at the joint terminal of the elongated rectangular feed line, and the connecting sheet is connected to the butterfly shaped radiator. A cylindrical conductor is erected on the joint hole of the elongated rectangular feed line, and the top end of the cylindrical conductor holds a clearance apart from the circular hole of the butterfly shaped radiator so as to adjust the bandwidth of the radiator.

A feed-in terminal is formed by penetrating the third dielectric substrate, and the feed-in terminal is in connection with a signal-receiving adapter formed on the upper surface of the third dielectric substrate so as to direct the signal to feed into the signal-receiving mode of the elongated rectangular feed line by induction.

BRIEF DESCRIPTION OF THE DRAWINGS

The drawings disclose the illustrative embodiments of the present invention, which serve to exemplify the various advantages and objects hereof, and are as follows.

DETAILED DESCRIPTION OF THE PREFERRED EMBODIMENT

Figure 1:
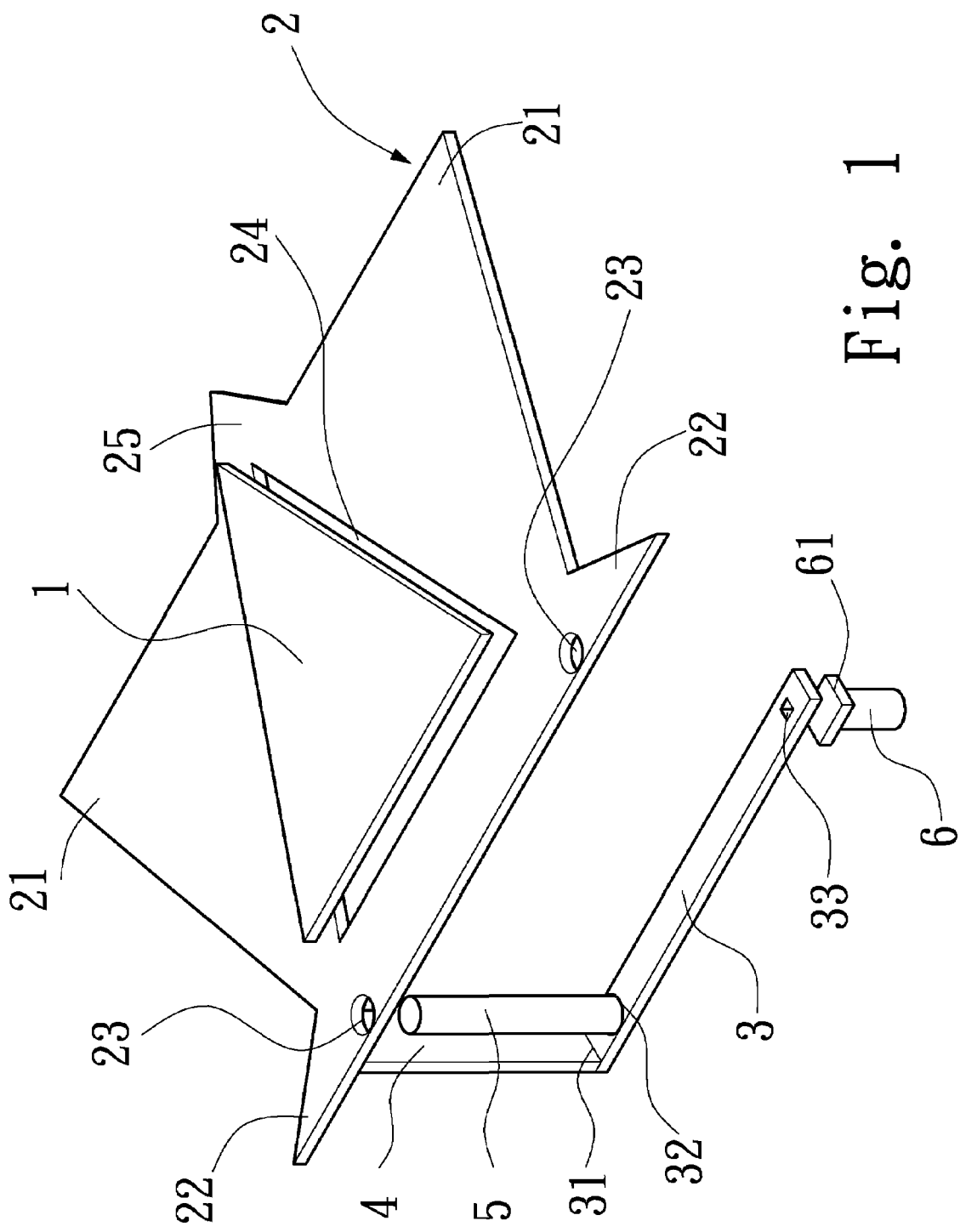
FIG. 1 is a three dimensional view of the left hand circularly polarized microstrip antenna according to the present invention.
Figure 2:
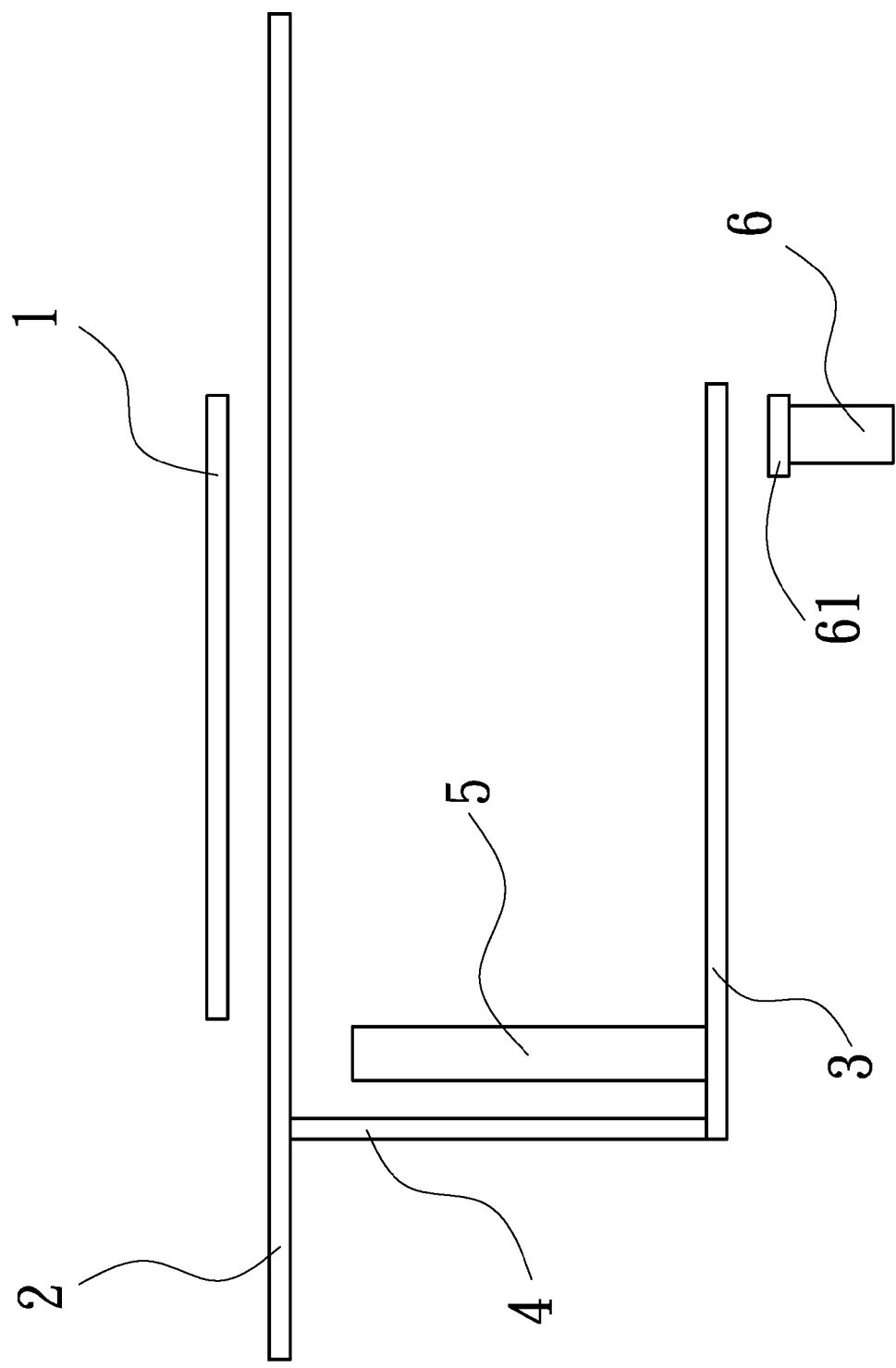
FIG. 2 is a front view showing the scheme of the left hand circularly polarized microstrip antenna according to the present invention.

Referring to FIG. 1 and FIG. 2, the butterfly shaped left/right hand circularly polarized microstrip antenna of the present invention has a first, second and third dielectric substrates disposed in the three dimensional space and comprises the following components: a delta resonator 1, a butterfly shaped radiator 2, an elongated rectangular feed line 3, a connecting sheet 4, a cylindrical conductor 5, a feed-in terminal 6, and a signal receiving adapter 61.

Figure 3:
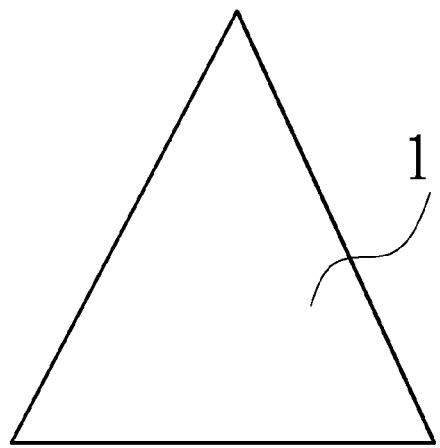
FIG. 3 is a plan view of the delta resonator according to the present invention.

Referring to FIG. 3, the delta resonator 1 is made by etching a conducting metallic substance and formed on the upper surface of the first dielectric substrate. The delta resonator 1 is configured into a triangular shape similar to, or approximately similar to a cavity 24 in the butterfly shaped radiator 2 and is disposed in parallel to the butterfly shaped radiator 2.

Figure 4:
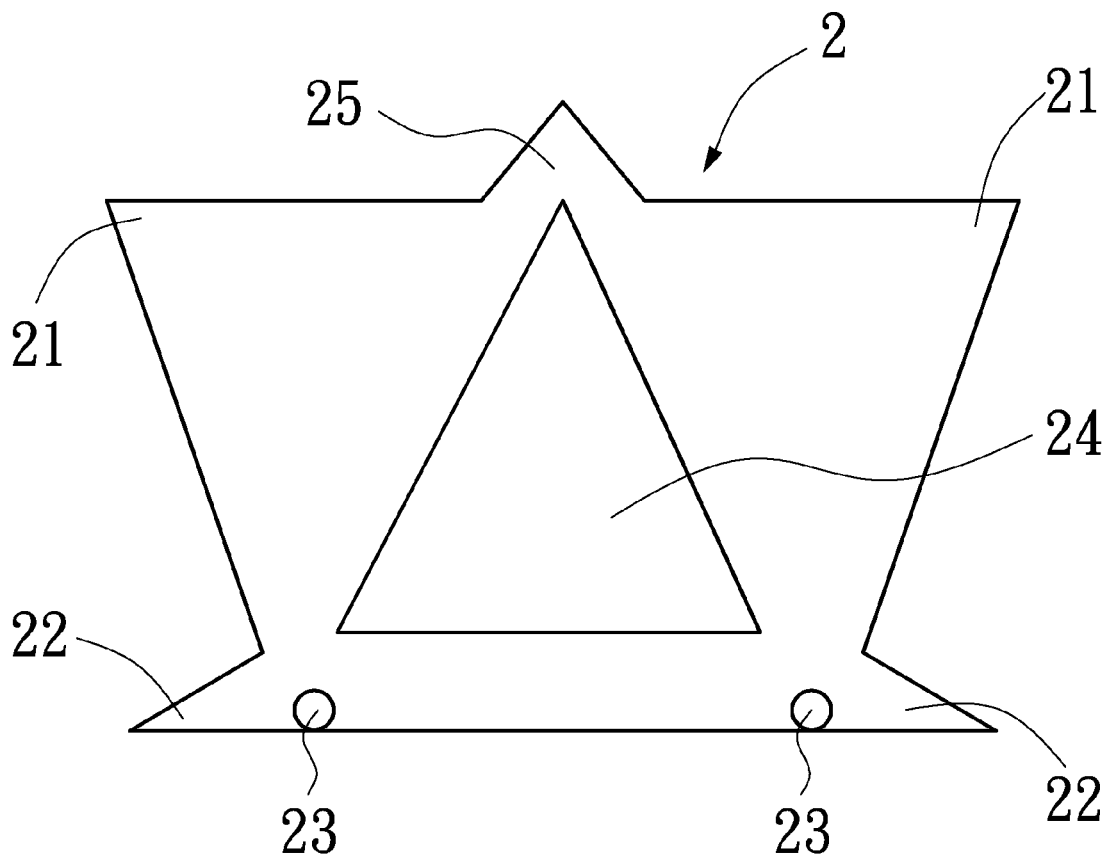
FIG. 4 is a plan view of the butterfly shaped radiator according to the present invention.
Figure 5:
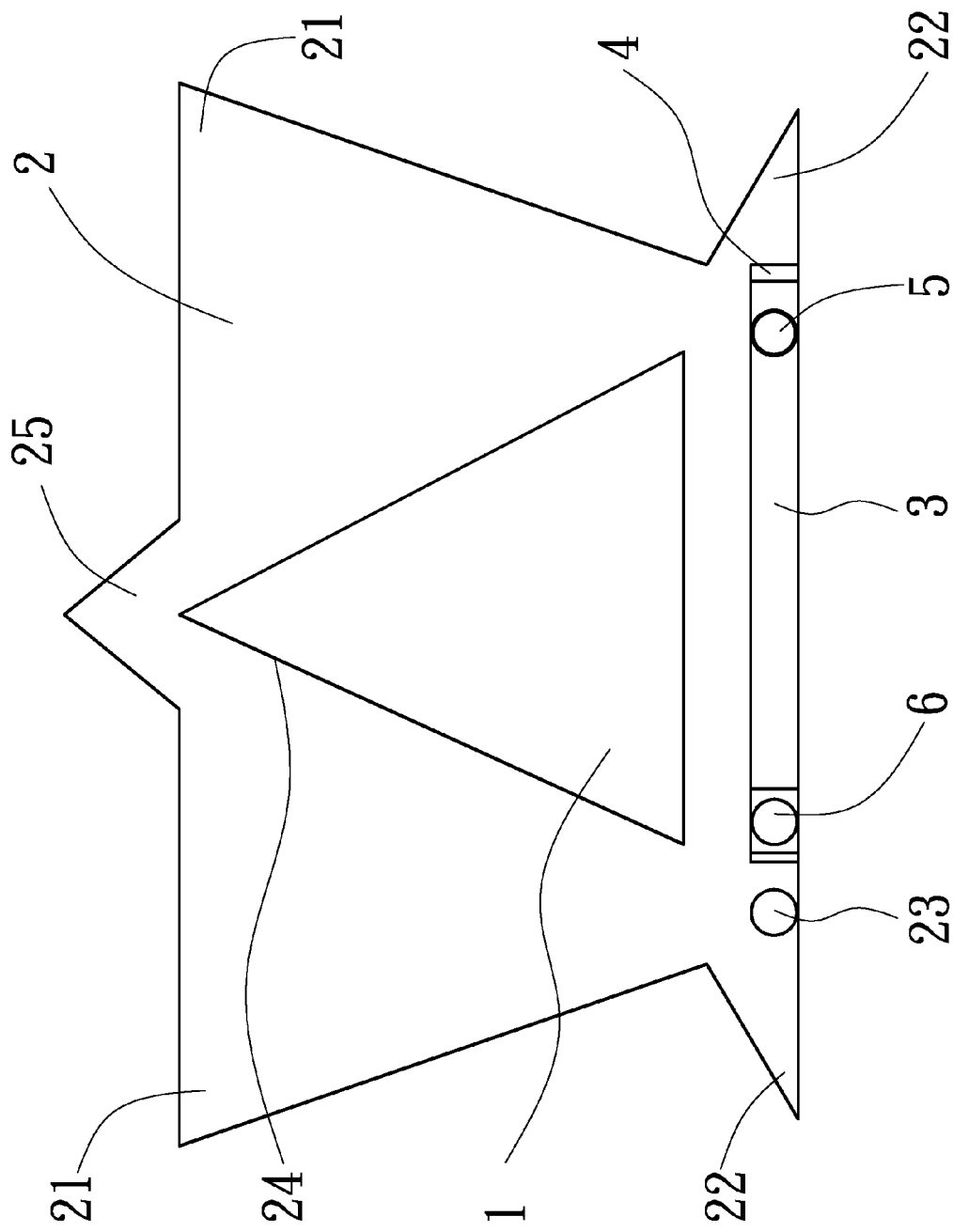
FIG. 5 is front view of the right hand circularly polarized microstrip antenna according to the present invention.

Referring to FIG. 4 and FIG. 5, the butterfly shaped radiator 2 is made by etching a conducting metallic substance and is formed beneath the lower surface of the first dielectric substrate. A pair of front wing tips 21 and a pair of rear wing tips 22 are respectively formed symmetrically at the two front side corners and the two rear side corners. Both front and rear wing tips 21 and 22 are formed into an acute angle. At least one circular hole 23 is formed between the two rear wing tips 22. The circular hole 23 is facing to the cylindrical conductor 5. The delta shaped cavity 24 is opened in the middle of the butterfly shaped radiator 2, and a vertex angle 25 is formed on the butterfly shaped radiator 2 in front of the cavity 24.

Figure 6:
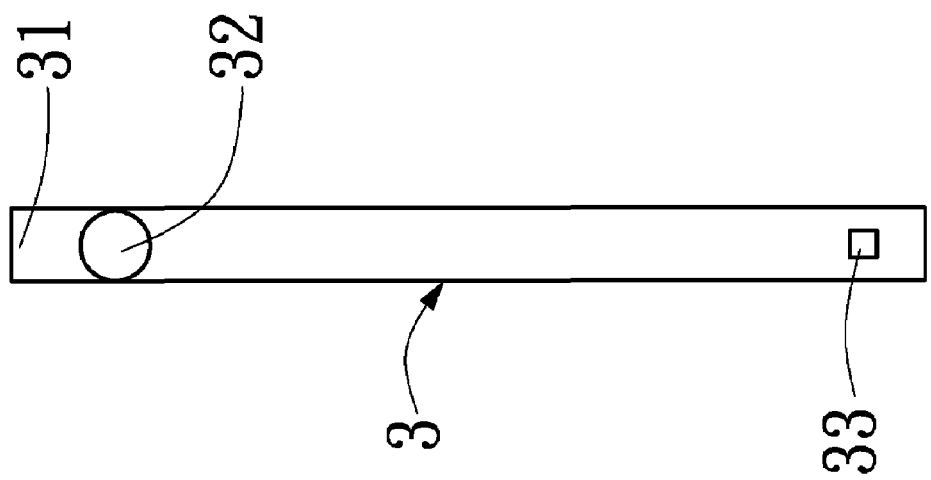
FIG. 6 is a plan view of the elongated rectangular feed line according to the present invention.

Referring to FIG. 6, the elongated rectangular feed line 3 is made by etching a conducting metallic substance and is formed on the upper surface of the second dielectric substrate, a joint terminal 31 and a joint hole 32 are formed at its one end, and a signal receiving node 33 is formed at the other end thereof so as to be electrically in connection with the butterfly shaped radiator 2 and the elongated rectangular feed line 3.

Figure 7:
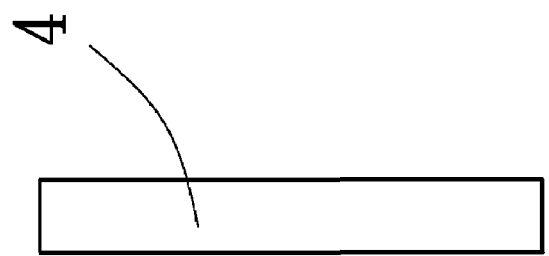
FIG. 7 is a plan view of the connecting sheet according to the present invention.

Referring to FIG. 7 and FIG. 1, the connecting sheet 4 is bridged between the joint terminal 31 of the elongated rectangular feed line 3 and the butterfly shaped radiator 2 so as to collaboratively form a microwave impedance transformer with the elongated rectangular feed line 3. The total length of the impedance transformer is less than quarter-wavelength, which is different from the traditional quarter-wavelength impedance transformer. This is one of the outstanding features of the present invention.

Figure 8:
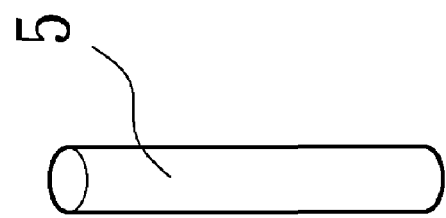
FIG. 8 is a perspective view of the cylindrical conductor according to the present invention.

Referring to FIG. 8 and FIG. 1, one end of the cylindrical conductor 5 is confined in a joint hole 32 of the elongated rectangular feed line 3, and the other end thereof is facing to a circular hole 23 of the butterfly shaped radiator 2 by keeping a proper space from the circular hole 23. The diameter and length of the cylindrical conductor 5 are made variable so as to allow the butterfly shaped radiator 2 capable of adjusting the impedance bandwidth. This is another outstanding feature of the present invention.

The feed-in terminal 6 is penetrating the third dielectric substrate, and is connected with a signal-receiving adapter 61 that is formed on the surface of the third dielectric substrate. Therefore, the signal by electromagnetic coupling means feeds into the signal-receiving node 33 of the elongation rectangular feed line. This is one more feature of the present invention. In this present invention. The wave signal is input or output feed-in the terminal 6. The feed-in terminal 6 can be employed a SMA terminal or a Type-N terminal.

Figure 9:
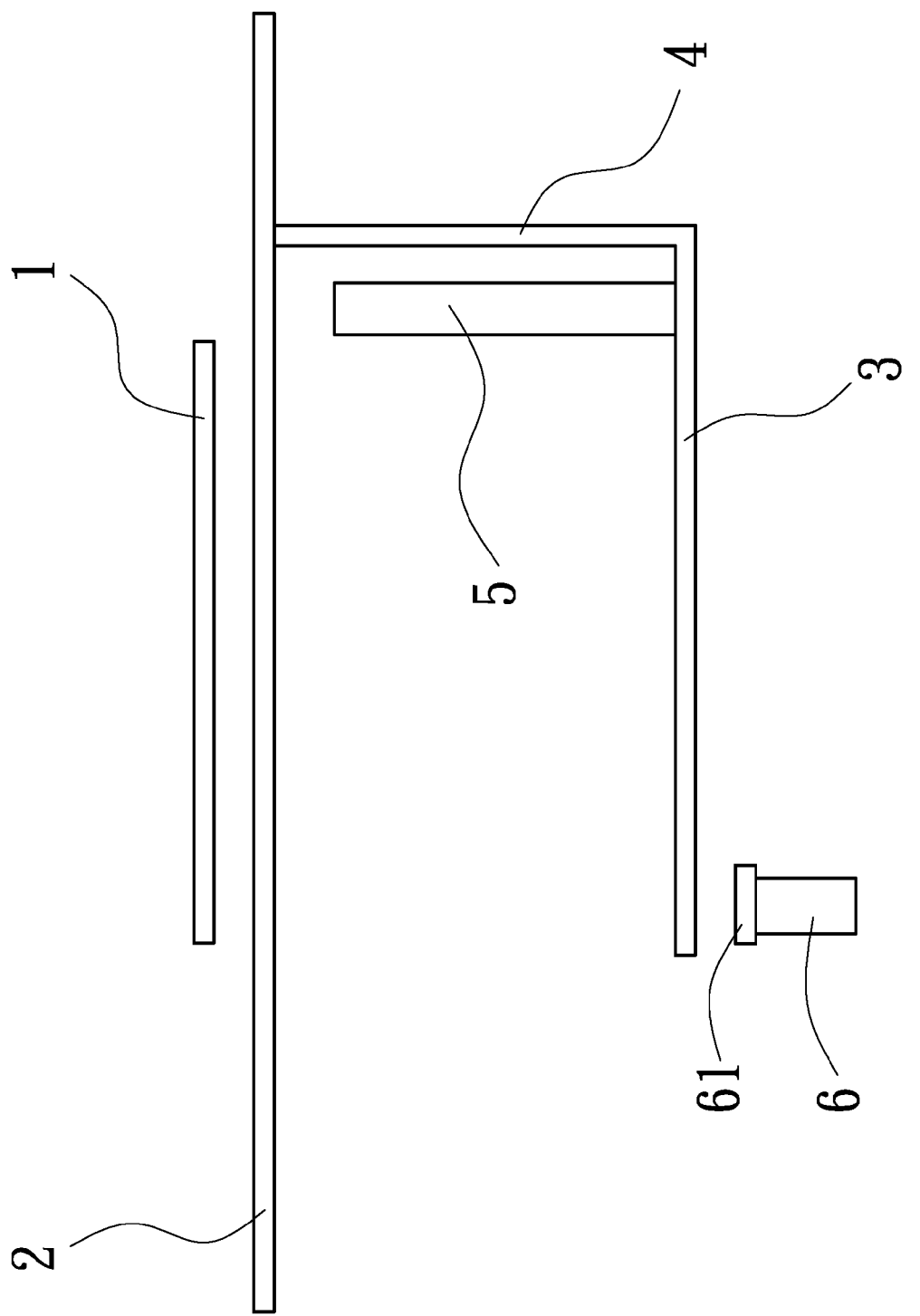
FIG. 9 is a side schematic view of the right hand circularly polarized microstrip antenna according to the present invention.

Referring to FIG. 9, in this side schematic view of the right hand circularly polarized microstrip antenna of the present invention, it is structurally different from the left hand one only the direction of disposition of the elongated rectangular feed line 3, the connecting sheet 4, the cylindrical conductor 5, the feed-in terminal 6, and the signal receiving adapter 61, other respects are identical.

All the dielectric substrates essentially belong to a printed circuit board (PCB), a FR4 board, or a RD board and stacked up in multiple layers so as to increase impedance and axial ratio of bandwidth. Basically, the thin conducting sheet, the conducting metal, or the thin conducting metal sheet are attached to the surface of the dielectric substrate by means of adherent or etching. After the signal is inputted (or outputted) to (from) the 50Ω feed-in terminal, the signal is further fed into the upper elongated rectangular feed line 3 by induction coupling instead of traditional direct coupling. By doing so, the demerit of the narrow bandwidth inherent to the traditional microstrip antenna is significantly overcome.

As the axial ratio of the bandwidth of a common circularly polarized microstrip antenna is relatively narrow, the present invention is put emphasis on improving the aforesaid shortcoming. Even though there has been developed means for improvement of the axial ratio of the bandwidth reported by certain international documents, the gain is not usually very satisfactory, besides, the wave beam is not always maintained in the wave propagation direction. As a matter of fact, the axial ratio and the signal-feeding angle of a circularly polarized antenna have a certain relation so that the signal is generally affected by the length and location of the feeder. Accordingly, the kernel of the present invention is to make the impedance matching circuit not to be limited by ¼ of wave length in case the signal is imputed to or outputted from a feed-in terminal. By doing so, the size of the matching circuit can be significantly reduced that results in reducing the size and the weight of an antenna.

As soon as the signal is input into the fed-in terminal 6, it is transmitted to the elongated rectangular feed line 3 in the way of induction coupling. The elongated rectangular feed line 3, when receiving the signal, can transmit it to the butterfly shaped radiator 2 via connecting sheet 4 by electromagnetic induction, and forming a wave beam between the butterfly shaped radiator 2 and the delta resonator 1 to radiate outwardly.

As the top end of the cylindrical conductor 5 is directly in contact with the butterfly shaped radiator, but instead, leaving a small clearance to allow the conductor 5 to vary its length and diameter so as to settle the modulated beam signal at a new position on the frequency spectra without deforming the wave beam and varying the mutual relationship among the component parts of the antenna. By doing so, the circularly polarized axial ratio of the bandwidth can be prominently improved, and the wave beam between the delta resonator 1 and the butterfly shaped radiator 2 can be delivered to the wave propagation direction and the reflection loss of the transmitted signal can also be effectively reduced thereby obtaining a broader impedance bandwidth.

Moreover, in order to obtain a broader impedance bandwidth and reduce the size of the matching circuit, the microstrip antenna of the present invention stacks up the dielectric substrates of the same or different thickness to increase thickness thereby widening the bandwidth.

Figure 10:
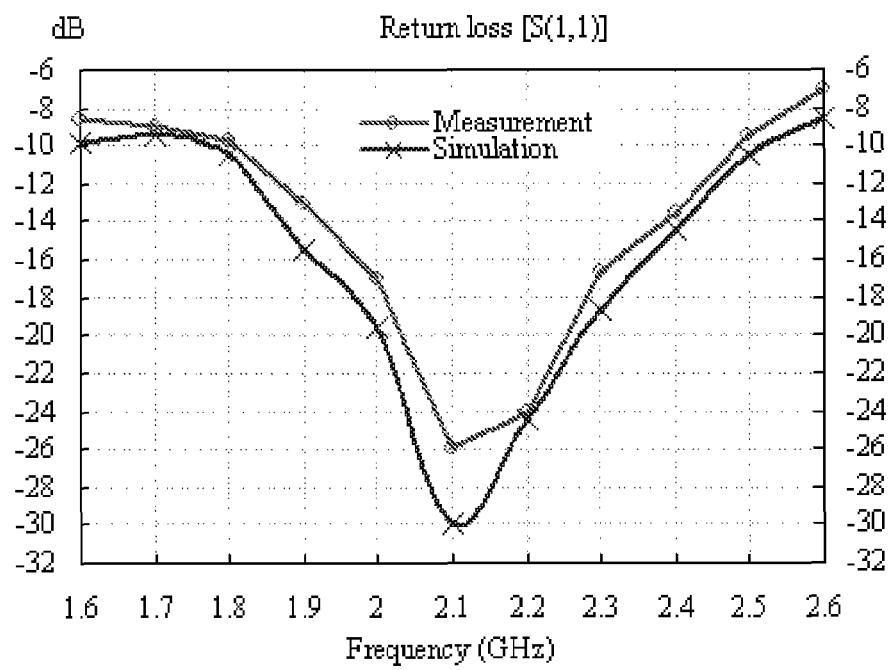
FIG. 10 is a graph of frequency VS return loss simulation and measurement curves according to the present invention.

Referring to FIG. 10 shows the variation of simulated and measured return loss with frequency of the present invention, the simulated and measured less than 10 dB RL impedance bandwidth about 33%, where the operational frequency is 2.1 GHz.

Figure 11:
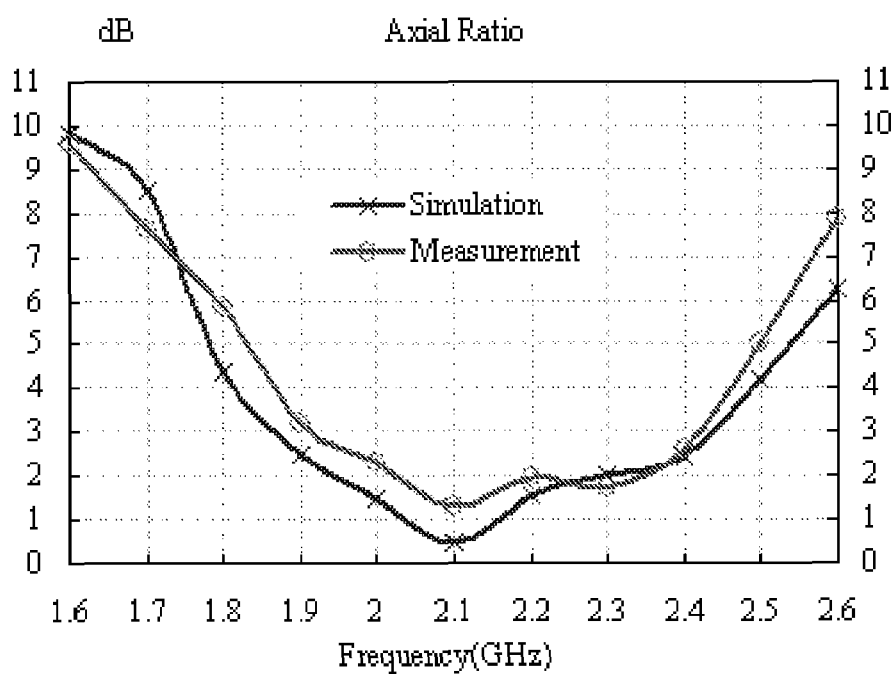
FIG. 11 is a graph of frequency VS axial ratio simulation and measurement curves of the antenna according to the resent invention.

Referring to FIG. 11, according to this graph of frequency vs. axial ratio simulation and measurement curves of the present invention, the axial ration is below 3 dB at the region of 55% center frequency 2.1 GHz.

Figure 12:
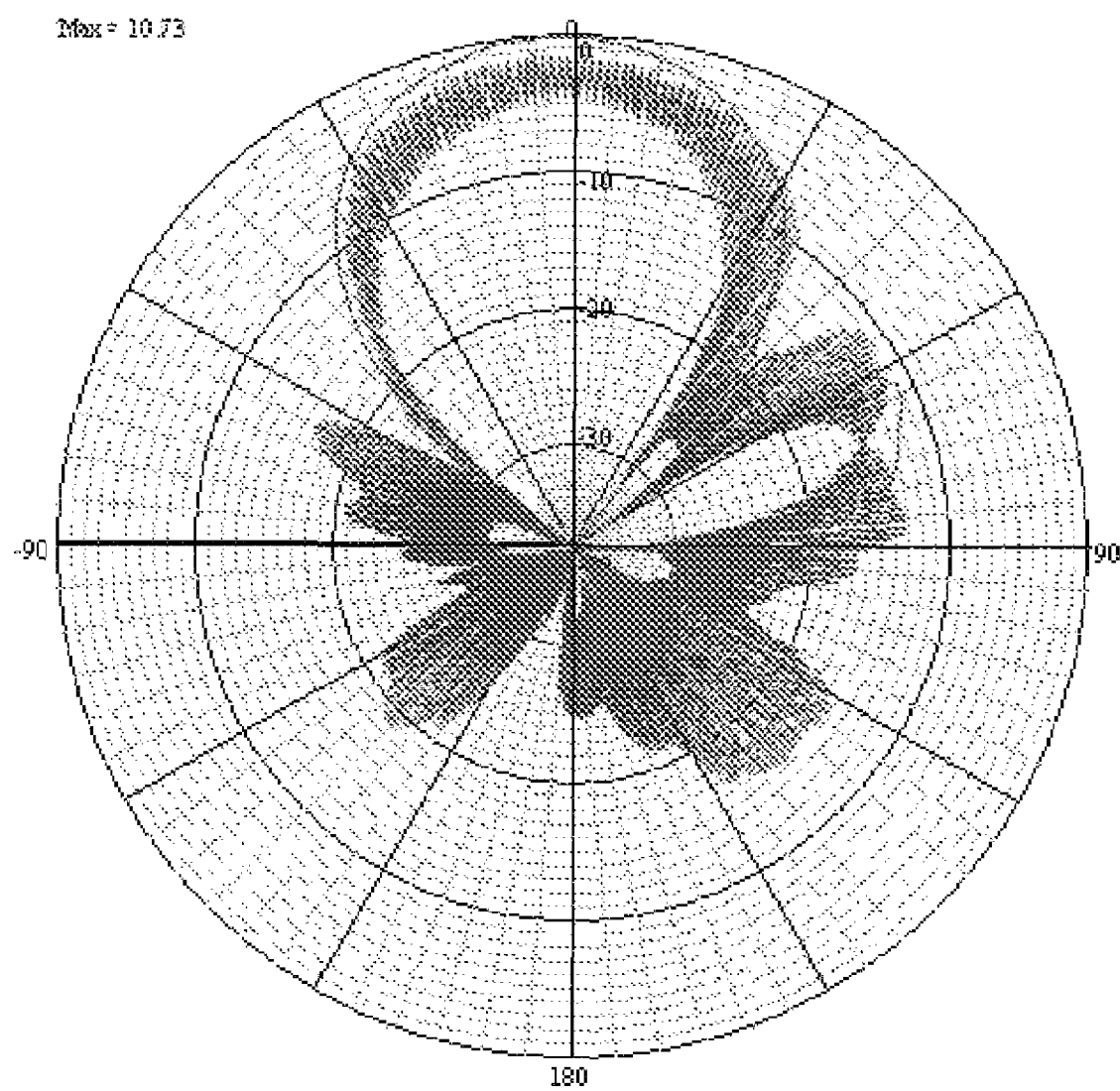
FIG. 12 is a graph of far field patterns of the axial ratio at frequency 2.1 GHz measured in Near-Far field measurement system of the anechoic chamber.

Referring to FIG. 12, this is a graph of far field patterns of the axial ratio at frequency 2.1 GHz measured in Near-Far field measurement system of the anechoic chamber for the present invention.

Figure 13:
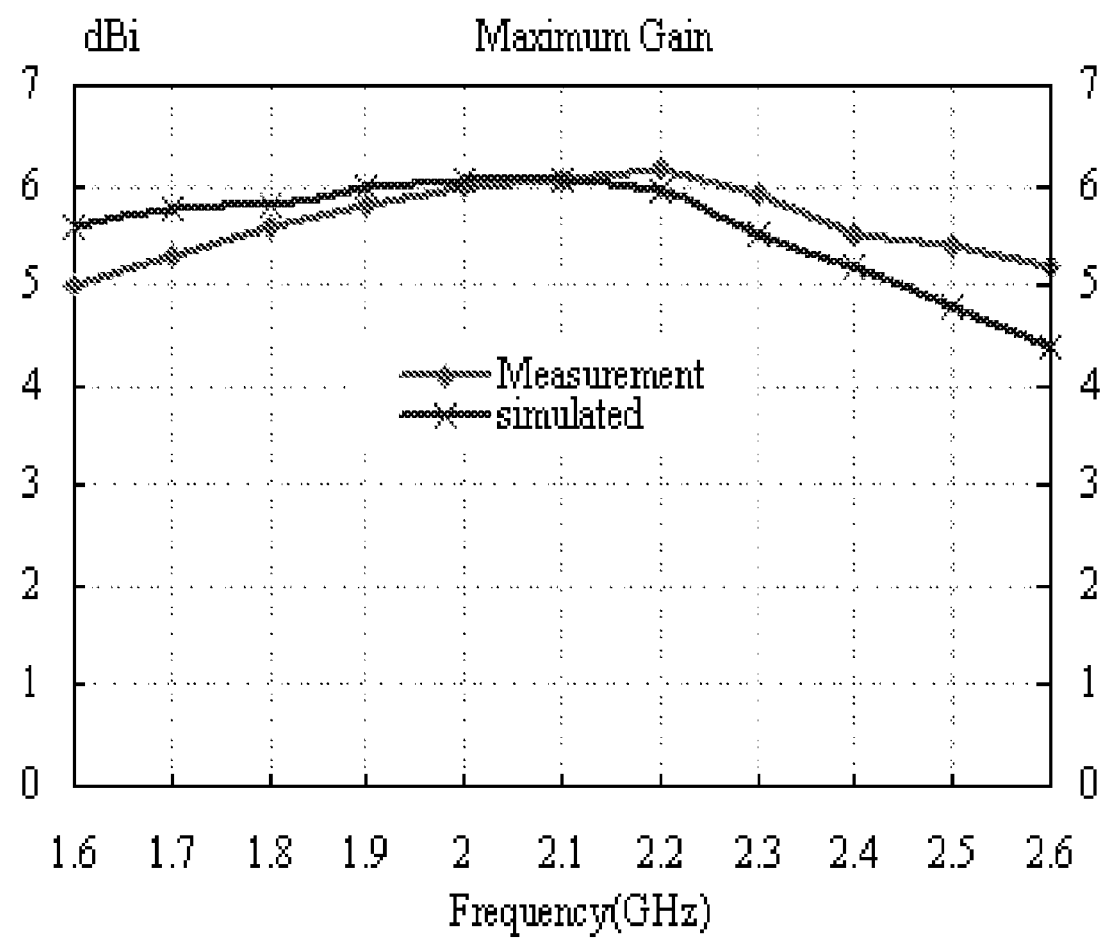
FIG. 13 is a graph of frequency vs. circularly polarized maximum gain of the antenna according to the present invention, simulated and actually measured.

In the present invention, the circularly polarized maximum gain is over 5 dBi at frequency 2.1 GHz from simulation and measurement as shown together in FIG. 13.

It is understood that the present invention is a high level technical creation and by no means, simply utilizes, conventional technology or knowledge known prior to the application for patent or can easily be made by persons skilled in the arts prior to the application for patent, therefore the present invention is submitted for applying patent.

Many changes and modifications in the above mention described embodiments of the invention can, of course, be carried out without departing from the scope thereof. Accordingly, to promote the progress in science and the useful arts, the invention is disclosed and is intend to be limited only by the scope of the appended claims.

What is claimed is:

1. A coupled feed-in butterfly shaped left/right hand circularly polarized microstrip antenna comprising:

a delta resonator;

a butterfly shaped radiator having a pair of front wing tips and a pair of rear wing tips respectively formed symmetrically at two front side corners and two rear side corners thereof, at least one circular hole being formed between said two rear wing tips, a delta shaped cavity being opened in the middle of said butterfly shaped radiator, and a vertex angle being formed on said butterfly shaped radiator in front of said delta shaped cavity;

an elongated rectangular feed line with a joint terminal and a joint hole formed at one end thereof, and a signal receiving node formed at the other end thereof;

a connecting sheet disposed at the joint terminal of said elongated rectangular feed line, and connected to said butterfly shaped radiator;

a cylindrical conductor erected on the joint hole of said elongated rectangular feed line with a proper space from the circular hole of said butterfly shaped radiator for adjusting the impedance bandwidth; and a feed-in terminal in connection with a signal receiving adapter so as to direct the signal to feed into said signal receiving node of said elongated rectangular feed line located above by induction.

2. The antenna of claim 1, wherein said front wing tip of said butterfly shaped radiator is formed into an acute angle.

3. The antenna of claim 1, wherein said rear wing tip of said butterfly shaped radiator is formed into an acute angle.

* * * * *